US00PP34716P2

(12) United States Plant Patent
Austin

(10) Patent No.: US PP34,716 P2
(45) Date of Patent: Nov. 8, 2022

(54) SHRUB ROSE PLANT NAMED 'AUSPITAL'

(50) Latin Name: *Rosa hybrida*
Varietal Denomination: AUSpital

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 17/300,857

(22) Filed: Nov. 29, 2021

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 5/0222
See application file for complete search history.

(56) References Cited

PUBLICATIONS

CPVO Citation as per 20212699 for 'AUSpital'; Dec. 15, 2021; 2 pages.*

* cited by examiner

*Primary Examiner* — Kent L Bell
(74) *Attorney, Agent, or Firm* — KPPB LLP

(57) ABSTRACT

A variety of rose plant of the shrub class, named 'AUSpital'. The 'AUSpital' is a variety of an uplifting, healthy, and robust medium sized, upright rose shrub bearing unusual, open cupped flowers of soft yellow, borne in well-spaced sprays having a light Myrrh fragrance.

1 Drawing Sheet

Classification: The present invention relates to a new *Rosa hybrida* shrub of the market class 'English Rose'.

Variety denomination: The new plant has the varietal denomination 'AUSpital'.

ORIGIN OF INVENTION

This invention relates to a new and distinct variety of shrub rose plant named 'AUSpital', which was originated from the cross-pollination of the two 'unnamed' and unpatented seedlings of *Rosa hybrida.*

BACKGROUND OF THE INVENTION

The primary objective of this breeding was to produce an uplifting, healthy, and robust medium sized, upright rose shrub bearing unusual, open cupped flowers of soft yellow, borne in well-spaced sprays having a light Myrrh fragrance.

SUMMARY OF THE INVENTION

Among the features which distinguish the new variety from others presently available and commercial rose cultivars known to the inventor are the following combination of characteristics: repeat flowering medium sized, double blooms of soft yellow bloom color with a light Myrrh fragrance and having very good disease resistance.

Asexual reproduction of the new variety by budding as performed in Albrighton, United Kingdom shows that the foregoing and other distinguishing characteristics come true to form and are established and transmitted through succeeding asexual propagations. 'AUSpital' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSpital' are two unnamed seedlings. The new rose may be distinguished from its seed parent, by the following combination of characteristics: the seed parent is of an apricot color compared to the yellow of 'AUSpital', has larger flowers, and has larger foliage when compared to 'AUSpital'. The new rose may be distinguished from its pollen parent, by the following combination of characteristics: the pollen parent is of an apricot color, has semi-double blooms as opposed to the double blooms of 'AUSpital', and is a much larger shrub when compared to 'AUSpital'.

COMPARISON WITH THE CLOSEST COMMERCIALLY AVAILABLE CULTIVAR

The closest commercially available cultivar to the new variety is an unpatented variety 'AUSeasel'. While both blooms are of soft yellow in color, 'AUSeasel' has an overall color of RHS 4D (yellow group), and 'AUSpital' has an overall color of RHS 10B (yellow group). The bloom diameter of 'AUSeasel' measuring at about 8 cm per bloom, is larger than that of 'AUSpital' measuring at about 5.75 cm. In addition, 'AUSeasel' has fewer petals of about 45 per bloom than 'AUSpital', which has about 54 petals per bloom. Finally, when the sepals first divide on a flowering bloom, 'AUSeasel' presents a color of RHS 60C (red group), with RHS 145C (yellow-green group), while 'AUSpital' has a color of RHS 12C (yellow group).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed. The illustration is of 7-year-old rose plants of the new variety.

DESCRIPTION OF THE NEW VARIETY

Observations of budded 'AUSpital' specimens were made at a nursery in Albrighton, Wolverhampton, United Kingdom. The following description is of 7-year-old rose plants of the new variety grown in a garden environment in Albrighton, United Kingdom in the month of July. Phenotypic expression may vary with environmental, cultural and climatic conditions, as well as differences in conditions of light and soil.

FLOWER CHARACTERISTICS:

Blooming habit: Recurrent. The number of blooms per plant during the growing season is profuse, but there are too many to count.

Bud:

- *Size*.—About 3 cm long and 2 cm in diameter when the petals start to unfurl.
- *Form*.—The bud form is pointed ovoid.
- *Color*.—When sepals first divide, the bud color is RHS 12C (yellow group). When half blown, the upper sides of the petals are RHS 2D (yellow group), and the lower sides of the petals RHS 2D (yellow group).
- *Calyx*.—Shape: star shape, with the sepals folding back against the stems. Length: 5.7 cm. Diameter: 5.7 cm.
- *Sepals*.—Arrangement: Regularly arranged. Color: Upper Surface: RHS 144C (yellow-green group). Lower Surface: RHS 144B (yellow-green group). Length: 2.7 cm. Width: 0.9 cm. Shape: Lanceolate. Margin: Glandular. Surface texture: Upper Surface: Hairy. Lower Surface: Glandular. Number: There are 3 lightly appendaged sepals, and 2 unappendaged sepals with glandular edges.
- *Receptacles*.—Color: RHS 143A (green group). Shape: Pear. Size: Medium to small, about 0.8 cm long×0.7 cm wide. Surface: Smooth.
- *Peduncle*.—Length: Medium, averaging about 6.7 cm. Diameter: about 0.2 cm to 0.3 cm. Surface: glandular. Color: RHS 144B (green group). Strength: Normal.

Blooms:

- *Size*.—Medium to small, average open diameter is about 5.75 cm.
- *Depth*.—About 2.75 cm.
- *Borne*.—Several together in clusters of 4-14 with blooms having a rounded shape.
- *Stems*.—Strength: Normal, average length is about 7 cm. Diameter: 0.3 cm.
- *Form*.—When first open, bloom is cupped. Permanence of bloom: outer petals curl back.
- *Flower type*.—Double bloom.

Petalage: Number of petals under normal conditions: 54.

- *Color*.—The upper sides of the petals are RHS 2D (yellow group). The reverse sides of the petals are RHS 2D (yellow group). The base of the petals has a small yellow spot that is RHS 6A (yellow group) in color.
- *Variegations*.—None.
- *Discoloration*.—The general tonality at the end of the first day is RHS 10B (yellow group), and at the end of the third day is RHS 10C (yellow group). As bloom ages, bloom fades to a tone of RHS 155D (white group).
- *Fragrance*.—Slight to moderate. Character of fragrance: Myrrh.

Petals:

- *Texture*.—Satiny on both sides. Size: Width: 2.7 cm. Length: 3.3 cm.
- *Surface*.—Smooth.
- *Shape*.—Obovate of inner petals and obcordate of outer petals.
- *Margin*.—Entire, with a notch on the obcordate petals.
- *Apex shape*.—Obcordate.
- *Base shape*.—Slightly acute.
- *Form*.—Incurved.
- *Arrangement*.—Informal.
- *Petaloids*.—Number: 0-5. Color: RHS 10C (yellow group). Length: 2 cm. Width: 0.5 cm. Shape: Obovate. Margin: Uniform.
- *Persistence*.—Petals drop off cleanly before drying.
- *Lastingness*.—On the plant: Fair about 4-7 days. As a cut flower: not tested.

Reproductive parts:

- *Stamens*.—Number: approximately 85. Length: approximately 0.3 cm.
- *Anthers*.—Length: approximately 0.2 cm. Color: RHS 5C (yellow group). Arrangement: Regular around styles.
- *Filaments*.—Color: RHS 13B (yellow group). Length: 0.7 cm-0.9 cm.
- *Pollen*.—Color: RHS 13B (yellow group). Amount: Scarce.
- *Pistils*.—Number: approximately 30. Length: approximately 0.7 cm.
- *Styles*.—Color: RHS 157D (green-white group). Length: 0.4 cm-0.5 cm.
- *Stigmas*.—Color: RHS 5C (yellow group). Length: 0.1 cm.
- *Hips*.—NONE Observed.

PLANT CHARACTERISTICS

Plant form: Shrub.

Plant growth: Medium and upright.

Age to maturity: 2 years.

Mature plant: Height: 100 cm. Width: 75 cm.

Rootstock: *Rosa dumetorum* 'Laxa' for the observed plants in the United Kingdom. 'Dr Huey' in the USA.

Foliage:

- *Number*.—Leaflets on normal mid-stem leaves is: 5 with instances of 7 (including terminal leaflet).
- *Size*.—Medium, about 14 cm long×10 cm wide.
- *Quantity*.—Abundant to normal. Number of leaves per flowering stem is: 7-10.

*Color*.—New foliage: Upper side: RHS 146B (green group). Lower side: RHS 144A (green group). Old foliage: Upper side: RHS 146A (green group). Lower side: RHS 146C (green group).

Leaflets:

*Size*.—About 5 cm long×4 cm wide.

*Shape*.—Pointed oval.

*Base shape*.—Cordate.

*Apex shape*.—Acuminate.

*Texture*.—Leathery.

*Glossiness*.—The glossiness of the upper side of the leaflet is weak. The glossiness of the lower side of the leaflet is dull and matt.

*Edge*.—Serrated.

*Serrations*.—Single.

*Petiole*.—Color: upper side is RHS 146C (green group), and reverse side is RHS 145A (green group). Length: 4 cm-6 cm. Width: 0.1 cm. Surface Texture: Glandular.

*Petiole rachis*.—Color: RHS 145A (green group). Length: about 2.5 cm to 3 cm. Diameter: about 0.1 cm to 0.2 cm. Upper Surface Texture: Slightly glandular. Underside: slightly glandular.

Stipules: Stipule is lateral and auricle. The shape is lanceolate with an acute apex. Length: 2.5 cm, serrated to glandular. Color: RHS 144B (green group).

*Auricle*.—Shape: Lanceolate. Length: 0.6 cm Width: 0.2 cm. Color: RHS 143A (green group).

*Vein color*.—RHS 146B (green group).

*Venation pattern*.—Reticulate.

Wood:

*New wood*.—Color: RHS 137D (green group). Bark: Smooth.

*Old wood*.—Color: RHS 144B (green group). Bark: Smooth.

Branching habit:

*Number*.—2-3 per main stem

*Dimensions*.—Length: 40-60 cm. Diameter: 0.6 cm-0.8 cm. .

Stems:

*Mature stem*.—Length: 80 cm-100 cm. Diameter: 0.6 cm-0.8 cm.

*Internode distance*.—5 cm-6 cm. The above measurements are all variable, depending on growing conditions in a season. Stem Pubescence Present: No.

Prickles:

*Quantity*.—Number per stem length: 5-10 per 10 cm. On laterals from main canes: ordinary. Number per stem length: 5-10 per 10 cm.

*Form*.—straight to deep concave.

*Length*.—0.5 cm.

*Color when young*.—Slightly translucent RHS 59B (red-purple group).

*Color when mature*.—RHS N199D (grey-brown group).

Small prickles:

*Quantity*.—Main stalk: Many. Number per stem length: 10 per 10 cm. Laterals: Many. Number per stem length: 10 per 10 cm. Color: When young: slightly translucent RHS 59B (red-purple group). When mature: RHS N199D (grey-brown group).

Disease resistance:

*Powdery mildew* (*podosphaera pannosa*).—Resistant.

*Downy mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class named 'AUSPITAL', substantially as herein shown and described.

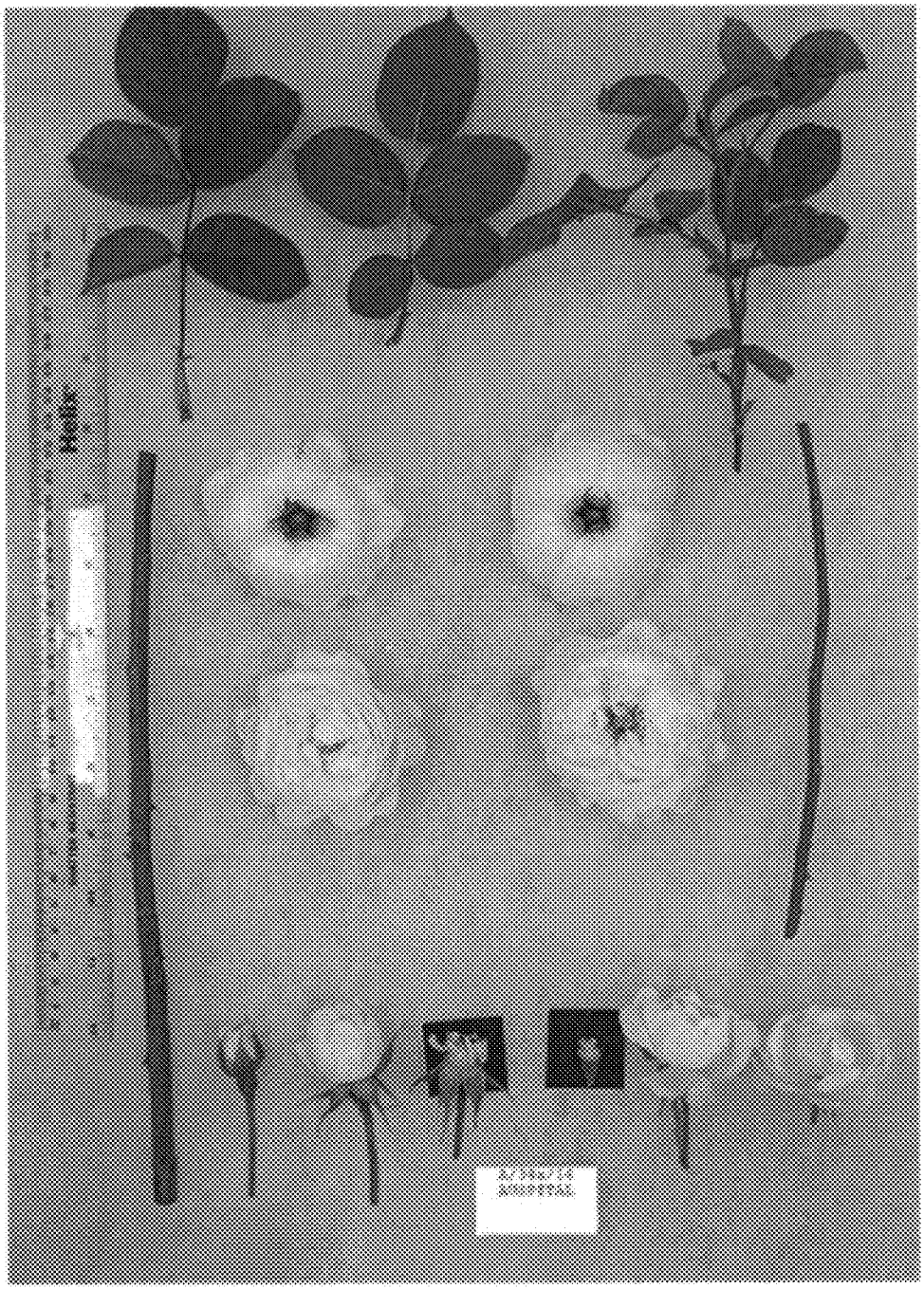

* * * * *